United States Patent
Borton et al.

(10) Patent No.: US 11,464,964 B2
(45) Date of Patent: Oct. 11, 2022

(54) NEURAL INTERROGATION PLATFORM

(71) Applicant: BROWN UNIVERSITY, Providence, RI (US)

(72) Inventors: David A. Borton, Pawtucket, RI (US); Marc Powell, Providence, RI (US)

(73) Assignee: Brown University, Providence, RI (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 16/530,619

(22) Filed: Aug. 2, 2019

(65) Prior Publication Data

US 2020/0038651 A1 Feb. 6, 2020

Related U.S. Application Data (60) Provisional application No. 62/714,565, filed on Aug. 3, 2018.

(51) Int. Cl.
| | | |
|---|---|---|
| *A61N 1/05* | (2006.01) | |
| *A61N 1/36* | (2006.01) | |
| *A61N 1/04* | (2006.01) | |
| *A61N 1/372* | (2006.01) | |
| *A61N 1/24* | (2006.01) | |

(52) U.S. Cl.
CPC ......... *A61N 1/0534* (2013.01); *A61N 1/0456* (2013.01); *A61N 1/0476* (2013.01); *A61N 1/0551* (2013.01); *A61N 1/24* (2013.01); *A61N 1/36028* (2013.01); *A61N 1/37276* (2013.01)

(58) Field of Classification Search
CPC .. A61N 1/0534; A61N 1/0456; A61N 1/0476; A61N 1/0551; A61N 1/24; A61N 1/36028; A61N 1/37276
See application file for complete search history.

(56) References Cited

U.S. PATENT DOCUMENTS

| | | | | |
|---|---|---|---|---|
| 3,867,950 A | * | 2/1975 | Fischell | A61N 1/3787 320/137 |
| 7,346,312 B2 | * | 3/2008 | Irazoqui-Pastor | H04B 1/04 455/349 |
| 7,991,475 B1 | * | 8/2011 | Tang | A61B 5/24 607/45 |

(Continued)

OTHER PUBLICATIONS

Aceros et al. "Polymeric Packaging for Fully Implantable Wireless Neural Microsensors", Engineering in Medicine and Biology Society (EMBC), 2012 Annual International Conference of the IEEE, 2012, pp. 743-746.

(Continued)

*Primary Examiner* — Carl H Layno
*Assistant Examiner* — Manolis Pahakis
(74) *Attorney, Agent, or Firm* — Adler Pollock & Sheehan P.C.

(57) ABSTRACT

A system includes spatially isolated nodes proximal to a cortical surface or spinal cord, a telemetric antenna array located above the dura, the telemetric antenna array configured to provide power to and exchange data with the spatially isolated nodes, and a power and data distribution unit configured to power the spatially isolated nodes, aggregate recorded data, send the aggregated recorded data and commands through a wireless link.

12 Claims, 6 Drawing Sheets

(56) References Cited

U.S. PATENT DOCUMENTS

| | | | | |
|---|---|---|---|---|
| 8,121,694 | B2* | 2/2012 | Molnar | A61B 5/4082 607/45 |
| 8,332,024 | B2* | 12/2012 | Rapoport | A61B 5/0031 330/261 |
| 8,380,314 | B2* | 2/2013 | Panken | A61N 1/3605 607/45 |
| 8,423,143 | B2* | 4/2013 | Bartic | B82Y 30/00 607/45 |
| 8,457,757 | B2* | 6/2013 | Cauller | A61N 1/3605 607/61 |
| 9,211,401 | B2* | 12/2015 | Frewin | A61B 5/24 |
| 9,387,320 | B2* | 7/2016 | Wingeier | A61N 2/006 |
| 9,662,498 | B1* | 5/2017 | Son | A61N 1/0531 |
| 9,691,873 | B2* | 6/2017 | Rogers | H01L 29/0669 |
| 10,265,530 | B1* | 4/2019 | Perryman | A61N 1/37264 |
| 10,386,360 | B2* | 8/2019 | Hickman | G01N 33/5061 |
| 10,432,025 | B2* | 10/2019 | Mirbozorgi | H02J 5/005 |
| 10,441,185 | B2* | 10/2019 | Rogers | A61N 1/0472 |
| 10,497,633 | B2* | 12/2019 | Rogers | H01L 23/22 |
| 10,603,493 | B2* | 3/2020 | Silva | A61N 1/0543 |
| 10,938,397 | B2* | 3/2021 | Smith | A61B 5/24 |
| 2003/0176905 | A1* | 9/2003 | Nicolelis | A61N 1/0529 607/116 |
| 2005/0143790 | A1* | 6/2005 | Kipke | A61B 5/24 607/60 |
| 2005/0187594 | A1* | 8/2005 | Hatlestad | A61N 1/3787 607/33 |
| 2006/0142803 | A1* | 6/2006 | Mintchev | A61N 1/36007 607/2 |
| 2006/0173259 | A1* | 8/2006 | Flaherty | A61B 5/24 600/331 |
| 2009/0182426 | A1* | 7/2009 | Von Arx | A61N 1/378 600/301 |
| 2010/0100010 | A1* | 4/2010 | Andarawis | A61B 5/0028 600/587 |
| 2010/0190229 | A1* | 7/2010 | Zhang | A61K 48/0058 435/173.1 |
| 2011/0054583 | A1* | 3/2011 | Litt | A61B 5/6852 600/377 |
| 2011/0230747 | A1* | 9/2011 | Rogers | A61B 5/05 600/377 |
| 2011/0307079 | A1* | 12/2011 | Oweiss | A61B 5/4094 623/27 |
| 2012/0165759 | A1* | 6/2012 | Rogers | H01L 23/3192 604/264 |
| 2012/0238855 | A1* | 9/2012 | Lanning | A61B 5/0017 600/378 |
| 2012/0283800 | A1* | 11/2012 | Perryman | G16H 20/30 607/60 |
| 2012/0296444 | A1* | 11/2012 | Greenberg | A61B 5/24 623/25 |
| 2013/0041235 | A1* | 2/2013 | Rogers | H05K 1/0283 600/386 |
| 2013/0066400 | A1* | 3/2013 | Perryman | A61N 1/37223 607/59 |
| 2013/0072775 | A1* | 3/2013 | Rogers | A61M 5/31 600/378 |
| 2014/0031607 | A1* | 1/2014 | Zilbershlag | A61N 1/3787 600/16 |
| 2014/0094674 | A1* | 4/2014 | Nurmikko | A61N 1/3787 607/45 |
| 2014/0257052 | A1* | 9/2014 | Muller | A61B 5/24 600/301 |
| 2014/0288393 | A1* | 9/2014 | Grevious | A61M 5/172 340/870.18 |
| 2015/0039054 | A1* | 2/2015 | Matos | A61N 1/3956 607/60 |
| 2015/0112233 | A1* | 4/2015 | Towe | A61N 1/3787 601/2 |
| 2015/0148878 | A1* | 5/2015 | Yoo | A61N 1/0456 607/118 |
| 2015/0153319 | A1* | 6/2015 | Shapiro | G01R 33/1284 324/207.11 |
| 2015/0157862 | A1* | 6/2015 | Greenberg | H05K 1/11 607/60 |
| 2015/0217120 | A1* | 8/2015 | Nandra | A61N 1/36185 607/59 |
| 2015/0223971 | A1* | 8/2015 | Zaveri | A61B 5/291 607/113 |
| 2015/0297900 | A1* | 10/2015 | Perryman | A61N 1/0553 607/60 |
| 2015/0351654 | A1* | 12/2015 | Kilsgaard | A61B 5/6846 600/377 |
| 2015/0373831 | A1* | 12/2015 | Rogers | H01M 50/502 29/829 |
| 2015/0380355 | A1* | 12/2015 | Rogers | H01L 29/78603 257/773 |
| 2016/0110643 | A1* | 4/2016 | Basu | G06N 20/00 706/22 |
| 2016/0278713 | A1* | 9/2016 | Shoaran | A61B 5/7232 |
| 2016/0339239 | A1* | 11/2016 | Yoo | A61N 1/36017 |
| 2017/0042474 | A1* | 2/2017 | Widge | A61B 5/0402 |
| 2017/0095667 | A1* | 4/2017 | Yakovlev | A61N 2/006 |
| 2017/0108926 | A1* | 4/2017 | Moon | A61N 1/0529 |
| 2017/0113046 | A1* | 4/2017 | Fried | A61N 1/36082 |
| 2017/0173345 | A1* | 6/2017 | Abiri | H02J 7/025 |
| 2017/0189699 | A1* | 7/2017 | Dellamano | H04B 5/0037 |
| 2017/0368330 | A1* | 12/2017 | Silay | A61N 1/36139 |
| 2018/0085605 | A1* | 3/2018 | Maharbiz | A61N 1/37205 |
| 2018/0165566 | A1* | 6/2018 | Rogers | G01J 1/429 |
| 2018/0185657 | A1* | 7/2018 | LeBaron | A61N 1/36125 |
| 2018/0236230 | A1* | 8/2018 | Pilly | A61B 5/16 |
| 2018/0333587 | A1* | 11/2018 | Howard | A61B 5/369 |
| 2018/0356771 | A1* | 12/2018 | Basu | A61F 2/72 |
| 2019/0038899 | A1* | 2/2019 | Lo | A61N 1/0551 |
| 2019/0053712 | A1* | 2/2019 | Rogers | A61B 5/0071 |
| 2019/0126047 | A1* | 5/2019 | Kassiri Bidhendi | A61N 1/36 |
| 2019/0275328 | A1* | 9/2019 | Zitnik | A61N 1/36053 |
| 2019/0374777 | A1* | 12/2019 | Burdick | A61N 1/36062 |
| 2020/0060607 | A1* | 2/2020 | Morgan | A61B 5/0031 |
| 2020/0222010 | A1* | 7/2020 | Howard | G06N 3/084 |
| 2020/0298005 | A1* | 9/2020 | Howard | A61B 5/686 |
| 2020/0315477 | A1* | 10/2020 | Constandinou | A61N 1/37229 |
| 2020/0405204 | A1* | 12/2020 | Howard | A61B 5/14546 |
| 2021/0059526 | A1* | 3/2021 | Khaleghi | H01Q 15/148 |
| 2021/0138249 | A1* | 5/2021 | Howard | G16H 20/30 |
| 2021/0162223 | A1* | 6/2021 | Kiani | A61N 1/0509 |
| 2021/0194289 | A1* | 6/2021 | Schulzetenberg | A61N 1/37223 |

OTHER PUBLICATIONS

Ahn et al. "Optimal Design of Wireless Power Transmission Links for Millimeter-Sized Biomedical Implants", IEEE Transactions on Biomedical Circuits and Systems, vol. 10, No. 1, Feb. 2016, pp. 125-137.

Bashkatov et al., "Glucose and Mannitol Diffusion in Human Dura Mater", Biophysical Journal, vol. 85, No. 5, 2003, pp. 3310-3318.

Biederman et al., "A Fully-Integrated, Miniaturized (0.125 mm) 10.5 WWireless Neural Sensor", IEEE Journal of Solid-State Circuits, vol. 48, No. 4, Apr. 2013, pp. 960-970.

Borton et al., "An Implantable Wireless Neural Interface for Recording Cortical Circuit Dynamics in Moving Primates", Journal of Neural Engineering, vol. 10, No. 2, Apr. 2013, 25 pages.

Bredeson et al., "Chronic In-Vivo Testing of a 16-Channel Implantable Wireless Neural Stimulator", 37th Annual International Conference of the IEEE Engineering in Medicine and Biology Society (EMBC), vol. 4, 2015, pp. 1017-1020.

Foster et al., "A Freely-Moving Monkey Treadmill Model", Journal of Neural Engineering, vol. 11, No. 4, Aug. 2014, 8 pages.

Gabriel et al., "The Dielectric Properties of Biological Tissues: III. Parametric Models for The Dielectric Spectrum of Tissues", Physics in medicine and biology, vol. 41, No. 11, 1996, pp. 2271-2293.

Ha et al., "Silicon-Integrated High-Density Electrocortical Interfaces", Proceedings of the IEEE, vol. 105, No. 1, Jan. 2017, pp. 11-33.

(56) References Cited

OTHER PUBLICATIONS

Harrison et al., "Wireless Neural Recording With Single Low-Power Integrated Circuit", IEEE Transactions on Neural Systems and Rehabilitation Engineering, vol. 17, No. 4, Aug. 1, 2009, pp. 322-329.

Ho et al., "Wireless Power Transfer to Deep-Tissue Microimplants", Proceedings of the National Academy of Sciences, vol. 111, Jun. 2014, pp. 7974-7979.

Jow et al., "Geometrical Design of a Scalable Overlapping Planar Spiral Coil Array to Generate a Homogeneous Magnetic Field", IEEE Transactions on Magnetics, vol. 49, No. 6, Dec. 2012, pp. 2933-2945.

Kiani et al., "A 13.56-mbps Pulse Delay Modulation Based Transceiver for Simultaneous Near-Field Data and Power Transmission", IEEE transactions on biomedical circuits and systems, vol. 9, No. 1, 2015, pp. 1-11.

Kiani et al., "Pulse Delay Modulation (PDM) A New Wideband Data Transmission Method to Implantable Medical Devices in Presence of a Power Link", 2012 IEEE Biomedical Circuits and Systems Conference (BioCAS), Nov. 2012, pp. 256-259.

Kim et al., "A 144-MHz Fully Integrated Resonant Regulating Rectifier with Hybrid Pulse Modulation for mm-Sized Implants", IEEE Journal of Solid-State Circuits, 2017, pp. 1-13.

Lee et al., "A Triple-Loop Inductive Power Transmission System for Biomedical Applications", IEEE Transactions on Biomedical Circuits and Systems, vol. 10, No. 1, 2016, pp. 138-148.

Lee et al., "Towards a Three-Phase Time-Multiplexed Planar Power Transmission to Distributed Implants", 2015 IEEE International Symposium on Circuits and Systems (ISCAS), 2015, pp. 1770-1773.

Liu et al., "Syringe-Injectable Electronics", Nature Nanotechnology, vol. 10, No. 7, Jul. 2015, pp. 629-636.

Mitz et al., "High Channel Count Single-Unit Recordings from Nonhuman Primate Frontal Cortex", Journal of Neuroscience Methods, vol. 289, Sep. 2017, pp. 39-47.

Montgomery et al., "Wirelessly Powered, Fully Internal Optogenetics for Brain, Spinal and Peripheral Circuits in Mice", Nature Methods, vol. 12, Aug. 2015, pp. 969-974.

Nagarkar et al., "Micro-Hermetic Packaging Technology for Active Implantable Neural Interfaces", Electronic Components and Technology Conference(ECTC), 2017 IEEE 67th. IEEE, 2017, pp. 218-223.

Najafi, Khalil., "Micropackaging Technologies for Integrated Microsystems: Applications to MEMS and MOEMS", International Society for Optics and Photonics, 2003.

Najafi, Khalil., "Packaging of Implantable Microsystems", Sensors, 2007 IEEE, Nov. 2007, pp. 58-63.

Poon et al., "Optimal Operating Frequency in Wireless Power Transmission for Implantable Devices", Annual International Conference of the IEEE Engineering in Medicine and Biology Society, 2007, pp. 5674-5679.

Powell et al., "An engineered home environment for untethered data telemetry from nonhuman primates", Journal of Neuroscience Methods, vol. 288, 2017, pp. 72-81.

Powell et al., "Toward Multi-Area Distributed Network of Implanted Neural Interrogators", Proc. SPIE 10352, Biosensing and nanomedicine X, 103520H (Aug. 29, 2017); https://doi.org/10.1117/12.2276046.

Scholvin et al., "Close-Packed Silicon Microelectrodes for Scalable Spatially Oversampled Neural Recording", IEEE Transactions on Biomedical Engineering, vol. 63, No. 1, 2016, pp. 120-130.

Schwarz et al., "Chronic, Wireless Recordings of Large Scale Brain Activity in Freely Moving Rhesus Monkeys", Nature methods, vol. 11, Issue 6, Jun. 2014, pp. 670-676.

Troyk et al., "Implantation and Testing of WFMA Stimulators in Macaque", 38th Annual International Conference of the IEEE Engineering in Medicine and Biology Society (EMBC), vol. 2016, Aug. 2016, pp. 4499-4502.

Viventi et al., "Flexible, Foldable, Actively Multiplexed, High-Density Electrode Array for Mapping Brain Activity in Vivo", Nature Neuroscience, vol. 14, No. 12, Nov. 2011, pp. 1599-1605.

Wellman et al., "A Materials Roadmap to Functional Neural Interface Design", Advanced Functional Materials, vol. 28, No. 12, 2017, 77 pages.

Xie et al., "Effect of Bias Voltage and Temperature on Lifetime of Wireless Neural Interfaces with Al2o3 and Parylene Bilayer Encapsulation", Biomedical Microdevice, vol. 17, No. 1, 2015.

Yin et al., "A 100-Channel Hermetically Sealed Implantable Device for Chronic Wireless Neurosensing Applications", IEEE Trans. on Biomedical Circuits and Systems, vol. 7, No. 2, Apr. 2013, pp. 115-128.

Yin et al., "Wireless Neurosensor for Full-Spectrum Electrophysiology Recordings during Free Behavior", Neuron, vol. 84, No. 6, Dec. 2014, pp. 1170-1182.

Zargham et al., "Maximum Achievable Efficiency in Near-Field Coupled Power-Transfer Systems", IEEE Transactions on Biomedical Circuits and Systems, vol. 6, No. 3, 2012, pp. 228-245.

\* cited by examiner

| Coil Parameter | Primary Coil | Secondary Coil |
|---|---|---|
| Sides | 6 | 4 |
| Apothem (mm) | 10.02 | 5 |
| Turns | 2 | 1 |
| Trace Thickness (μm) | 35.56 | 35.56 |
| Trace Width (mm) | 0.3 | 0.33 |
| Trace Separation (mm) | 0.7 | N/A |
| Substrate Material | Polyimide | FR4 |
| Substrate Thickness (mm) | 0.025 | 1mm |

NEURAL INTERROGATION PLATFORM

CROSS REFERENCE TO RELATED APPLICATIONS

This application claims benefit from U.S. Provisional Patent Application Ser. No. 62/714,565, filed Aug. 3, 2018, which is incorporated by reference in its entirety.

STATEMENT REGARDING GOVERNMENT INTEREST

None.

BACKGROUND OF THE INVENTION

The present invention relates generally to neurology and neuroscience, and more particularly to a neural interrogation platform.

In general, neurology is the branch of medicine concerned with the study and treatment of disorders of the nervous system. The nervous system is a complex, sophisticated system that regulates and coordinates body activities, and a complex network of functionally connected groups of cells which communicate to process information and generate behavioral outputs that allow us to navigate our environment. However, commercially available technologies struggle to probe all of these connected sub-domains with single-cell resolution. Electroencephalography and magnetic resonance imaging (MRI) capture activity across multiple areas, but have poor spatial resolution. Traditional microelectrode arrays (MEAs) can record individual cells but from a small, millimeter scale region of the brain. Attempts to scale MEA technology to record from more channels are hindered by tethered electronics or bulky connectors which introduce a geometric limit on the number of arrays which can be implanted safely in a clinical setting. Additionally, wire tethers used to connect an MEA to recording electronics are difficult to implant, must transverse the dura matter preventing it from fully healing, and introduce a mechanical leash which can cause the array to shift as the brain moves relative to the rest of the body. Importantly, efforts have been made in recent years to solve each of these problems, resulting in creative new neural probes or even complete devices for neural interfacing. However, neural probe designers often do not have a robust way to communicate with their interface and system designers target a single specific probe resulting in an inefficient 1:1 development strategy for neural interface systems with a given neural probe. Since new backend electronics must be developed for new probe technologies, development is slow.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features a system including spatially isolated nodes proximal to a cortical surface or spinal cord, a telemetric antenna array located above the dura, the telemetric antenna array configured to provide power to and exchange data with the spatially isolated nodes, and a power and data distribution unit configured to power the spatially isolated nodes, aggregate recorded data, send the aggregated recorded data and commands through a wireless link.

In another aspect, the invention features a method including recording data from spatially isolated nodes untethered from external electronics using a telemetric antenna array to wirelessly power and regulate the spatially isolated nodes.

In still another aspect, the invention features a system including spatially isolated nodes proximal to a cortical surface or spinal cord, each of the spatially isolated nodes configured to implement data analysis, data compression, closed loop stimulation and power saving control schemes, a telemetric antenna array located above the dura, the telemetric antenna array configured to provide power to and exchange data with the spatially isolated nodes, and a power and data distribution unit configured to power the spatially isolated nodes, aggregate recorded data, send the aggregated recorded data and commands through a wireless link.

Embodiments of the invention may include one or more of the following advantages.

The present invention leverages near-field inductive coupling techniques and a flexible system architecture to create a platform technology which can easily and simultaneously access multiple areas of the brain and enables neuroscientists and clinicians to mix and match different neural probes to suit their individual needs.

The present invention provides a platform for simultaneous multi-site neural recording that eliminates transdural cables, reduces surgical implantation site limitations, limits cortical damage due to micromotion between the neural interface and the skull, and removes the most likely pathway for long-term infection directly to the meninges (e.g., the cable).

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

DETAILED DESCRIPTION

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As described above, the present invention leverages near-field wireless communication techniques and a flexible system architecture to create a platform technology which can easily and simultaneously access multiple areas of the brain and enables neuroscientists and clinicians to mix and match different neural probes to suit their individual needs. Distributed, self-contained nodes float on the cortical surface and are equipped with electronics for full broadband neural data acquisition and stimulation for up to 128 channels, a programmable controller for on-board prototyping of processing algorithms, and wireless powering and communication. Each node is hermetically sealed for chronic implantation with individual package feedthroughs for each electrical channel. Importantly, the packaged electronics are independent of the type of electrodes which may be bonded to the electrical feedthroughs. In this way, as new neural probes are developed, probe designers need only to connect their interfaces to a node and can leverage the rest of the system to robustly communicate with their device thus resulting in significantly faster development times.

An array of inductive coils is placed epidurally and used to send wireless power and data to each of the implanted nodes. Without the need for transdural wiring, nodes can float with the brain's movements making a robust platform that does not suffer from the same limitations listed above for tethered micro-electrode arrays (MEAs). The antenna array is designed using overlapping coils making the system agnostic to surgical placement of the nodes and is robust to node movement. Therefore, the system can support multiple implanted nodes which are spatially isolated across distal brain regions. Without tethering, the nodes are easier to implant than traditional MEAS. The antenna array, encapsulated in an elastomeric polymer, mechanically resembles ECoG grids which are routinely implanted in human patients. Thus, there is precedence for the surgical techniques required to implant the device making it a viable architecture for future clinical indication.

On-board electronics are re-programmable while the nodes are still implanted. New algorithms such as data compression or low power system control can be tested on-the fly, allowing for continuous device updates. New research paradigms are also enabled as researchers gain the capability to run closed loop algorithms for either neural recording or stimulation at the interface itself. By eliminating significant latencies for communicating neural data using onboard computation, studies about fast time scale neural processes such as time-dependent plasticity or fast communication between cortical regions can be now be studied.

Figure 1:
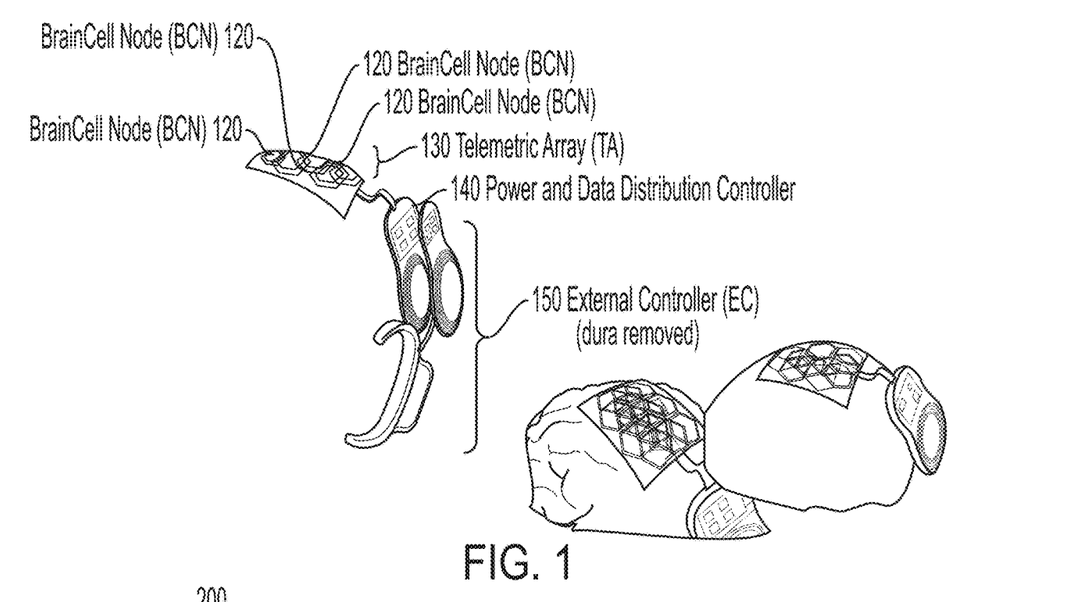
FIG. 1 is an exemplary system architecture.

FIG. 1 illustrates an exemplary system architecture 100. Spatially isolated nodes 120 are implanted on the cortical surface and receive power and data from a telemetric antenna array 130 located above the dura. A power and data distribution unit 140 powers the nodes while aggregating all the recorded data and sending them through a wireless optical link to an external controller 150 which is mounted to the patient's ear.

Traditionally, when new neural probes are developed, a full device ecosystem must also be developed to support communication with the probe, thus increasing the time and money needed to implement a new probe design. For this reason, many potentially useful designs are never brought to realization. The flexible electronic payload and modular architecture of the present invention provides a unique platform technology that enables new probe designs to be tested easily without additional development. Probe designers need only to bond their interface to a node 120 and can take advantage of all the system's features to test their design. While other floating "node-like" neural interfaces have been designed, many do not implement designs which facilitate multi-area distribution of the nodes 120. Other devices have limited data telemetry bandwidth or focus on only electrical stimulation. The design 100 specifically supports distributed nodes 120 each capable of transmitting high data rates and receiving enough wireless power from the antenna array 130 to support the capable electronics.

A field programmable gate array (FPGA) provides a unique opportunity for end-users to modify their use of the device. Each node 120 can implement data analysis, data compression, closed loop stimulation, power saving control schemes, or other algorithms that expand the usefulness of the device and potentially uncover new techniques that could be used on future neural implants. Other devices which implement a FPGA do not utilize it in such a flexible role. Such a design enables new research paradigms, expanding its market even to labs which may already employ other neural interfaces. It also allows for a deeper level of control over the implant for clinicians, and an ability for on-the-fly firmware updates.

Recently, fully implanted neural interfaces have been developed but either use titanium packaging which can be bulky and does not lend itself to wireless communication, or use polymeric encapsulation, which is not useful for chronic implants due to ionic diffusion over time. Each node 120 in the system 100 uses glass packaging technology which is both RF and optically transparent and robust to ionic diffusion making a low profile hermetic seal which is suitable for long term implants.

Each implanted node 120 need not implement the same probes, are agnostic to surgical placement, and robust to small implant movements. The platform 100 is ideal for mixing different probe types such as micro-electrode arrays, micro-ECoG grids, deep brain electrodes, and others to acquire a diverse set of signals from many parts of the brain.

The system 100 is useful across multiple domains and therefore is potentially viable in several different markets. It is useful as a research tool since it allows for easy implantation of several biological interface nodes which are spatially isolated. For example, interactions between distally located regions such as motor, visual, and pre-frontal cortices or between both cortical hemispheres can be studied using the same implant. The system 10 is useful as a platform for engineers to test new probe technologies, or on-board processing algorithms. Finally, as the technology matures and the range of compatible probes grows, clinicians can use system 100 to implement large-scale, multi-modal biological sensing and stimulation. For example, it can be used to facilitate existing technologies such as deep brain stimulation and epilepsy monitoring using ECoG, but also make more cutting-edge interfaces such as MEAs more accessible in the clinical domain, since the nodes are easier to implant than tethered MEAs and can move with the brain making them safer for human use.

Figure 2:
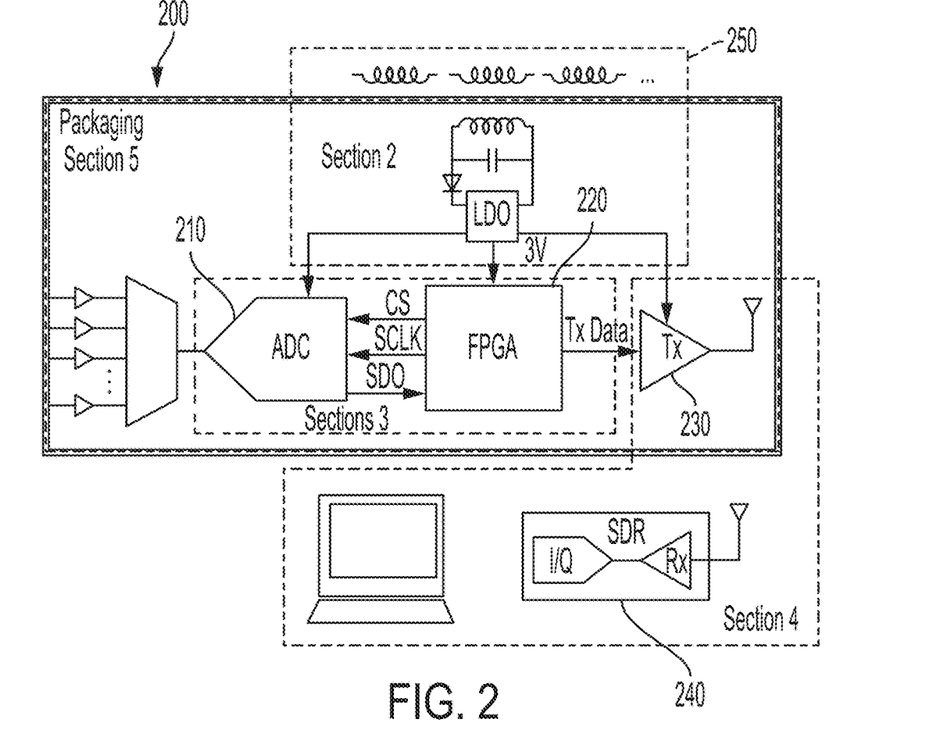
FIG. 2 is an exemplary block diagram.

In FIG. 2, an exemplary block diagram 200 illustrates the various modular components of the system 100 (of FIG. 1). It should be appreciated that other implementations may be employed in building the system 100 and that block diagram 200 is just one example implementation. All components of a node are wirelessly powered using a transdural inductive link enabling them to be positioned anywhere on the cortical surface. An ADC 210 digitizes multiple channels of amplified neural signals, an FPGA 220 captures the data and packetizes them for wireless transmission. A 3.5 GHz OOK RF transmitter 230 ASIC telemeters the data wirelessly to an SDR computer-in-the-loop receiver 240 which demodulates and interprets the signal.

Figure 4:
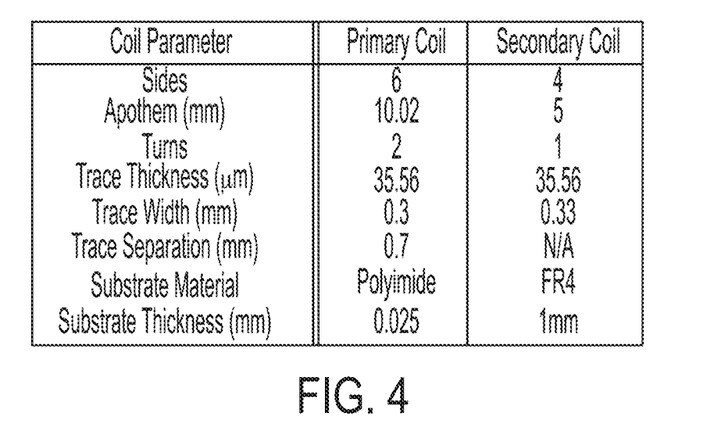
FIG. 4 illustrates a table.

A wireless power transfer subsystem 250 includes inductive coils designed to transfer wireless power to neural interrogators. A feature of the platform 100 is a desire to be agnostic to the placement of individual neural interrogator nodes on the cortical surface. To achieve this, a flexible array of coils resides above the dura and conforms to the cortical surface. Nodes, implanted subdurally, may then be placed anywhere underneath the antenna array, which maintains a coil density high enough to ensure that there will always be an inductor (coil) with minimal misalignment to each implanted node. By positioning the telemetric array 130 just above the dura, power transfer occurs over a very short distance and can therefore take advantage of high coupling coefficients between the coils. Choosing an appropriate design for the primary and secondary coils is essential for providing sufficient power to each node and must account for the electromagnetic interactions with the surrounding tissue. The diameter of the secondary coil is limited by the size of the node. Each primary coil in the telemetric array 130 should be large enough to cover as much surface area of the brain as possible and to limit overall array complexity, yet small enough to maintain strong coupling with a given node. In addition, their shape must allow multiple primary coils to be packed closely together in the array. Based on these restrictions, in this implementation, the secondary coil is chosen to be a 1×1 cm, single turn, square coil, and the primary coil was chosen to be a 2-turn, hexagonal coil with a 10 mm apothem. FIG. 4 illustrates Table 1, which details the dimensions of both coils.

Figure 3:
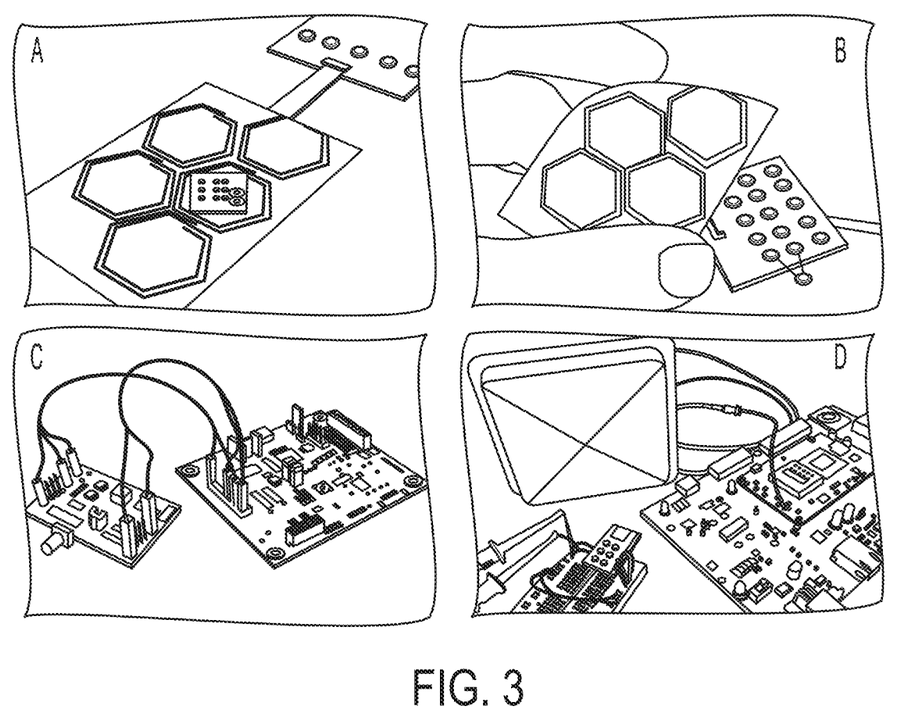
FIG. 3 illustrates exemplary fab devices.

Initial prototypes of the primary and secondary coils were fabricated using standard printed circuit board manufacturing techniques (PCB Minions, Princeton, N.J.). The nodes included a coil and circuitry for power rectification and regulation. To approximate the flexibility of the final telemetric array design, a single layer of five adjacent primary coils was fabricated on a flexible polyimide substrate and connected to a separate board containing the tuning circuitry. In FIG. 3, (A) illustrates an example prototype of a node containing power rectification and regulation circuitry with an example resistive load of 603. The node can be powered by a multi-coil telemetric array of hexagonal coils. (B) illustrates a prototype of the flexible telemetric array. The antenna array is surgically placed above the dura and conforms to the cortical surface. (C) illustrates development boards for the ADS7042 ADC and iCE40UL1K FPGA used to validate the neural signal collection path. These chips are integrated into a node approximately 1×1 cm. (D) illustrates an RF transmitter ASIC with an ultra-wide band antenna for sending neural data wirelessly, along with a receiver built using a receive antenna and a software defined radio.

Many studies have shown that maximum wireless power transfer efficiency is achieved when both primary and secondary coils are tuned to resonate at the same frequency using capacitors. The optimum frequency selection for small (mm scale) implants has been widely debated. High frequencies, near 1.5 GHz, allow for larger energy densities to be transferred to millimeter scale devices in deep tissue. However, at these frequencies, significant losses due to tissue absorption can occur. Since the nodes are implanted on the cortical surface and not deep within the tissue, cm scale coils can be used, reducing the required resonant frequency. In addition, as coil diameter and inductance increases, or as parasitic capacitance from component packages or coil turns are added to the circuit, it becomes more difficult to tune the inductor using reasonably sized external capacitors.

Power transfer efficiency (PTE) was measured using a single coil on the telemetric array, stimulated at the chosen resonant frequency of 48.4 MHz. A node was placed over the coil and the output voltage of the on-board 3V low dropout regulator (LDO; LD39020; ST-Microelectronics, Geneva, Switzerland) was measured across a 603Ω load. This load was chosen to assess the circuit's ability to deliver up to 15 mW of power to the active electronics on each neural interrogator. The capability to deliver >10 mW of power demonstrates a key benefit of the proposed transdural design. Since the system only needs to transfer power across the dura, sufficient power can be transmitted to support flexible circuit design, not limited to custom ultra-low power electronics.

Figure 5:
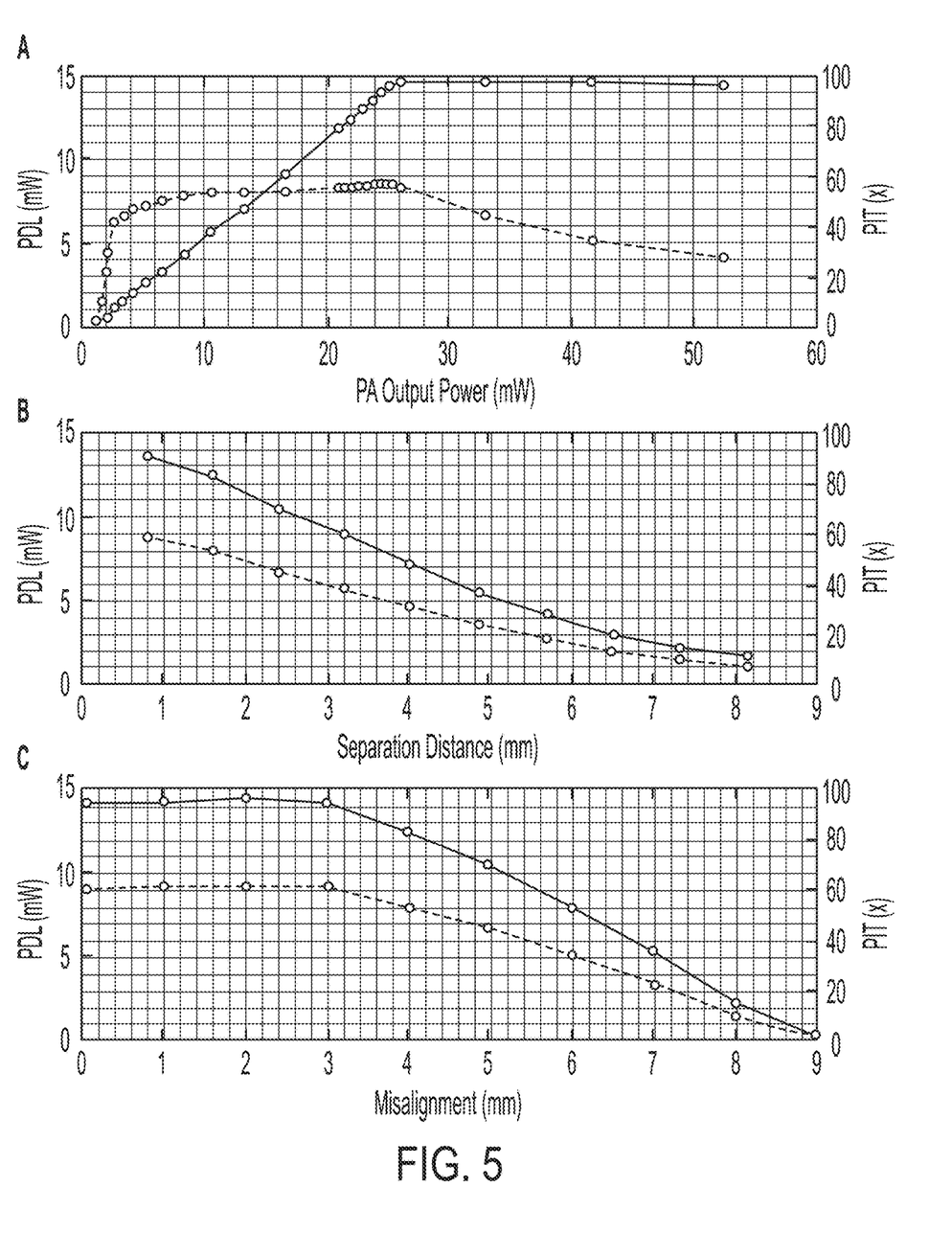
FIG. 5 illustrates exemplary plots.

In FIG. 5, plots of power delivered to load (PDL) and power transfer efficiency (PTE) of the wireless power transmission from one coil of the telemetric array to an individual node for various (A) PA output powers, (B) coil separation distances, and (C) coil misalignment distances are shown. Our system takes advantage of high coil coupling by ensuring that a node will always be both close to, and aligned with, at least one coil on the telemetric array.

Both the power delivered to the load (PDL) and PTE were calculated for various power amplifier (PA) outputs, coil separation distances, and coil misalignment distances Here, PTE was defined as $$PTE = P_{load}/P_{PA}$$

where $P_{load}$ is the power delivered to the load and $P_{PA}$ is the power output of the PA as measured using a spectrum analyzer with 50Ω input impedance. Since the input impedance of the telemetric array may be different than 50Ω and will vary depending on coupling with the node, actual power delivered to the array during testing should be less than this estimation. Therefore, PTE calculations given here are a conservative estimate of the final system's capability. As can be seen in FIG. 5A, both PDL and PTE increase with increasing transmitter power, until the regulation voltage of the LDO is reached and no further power can be delivered to the load. This saturation occurs at an output power of 25.12 mW (14 dBm) and also represents the point at which the target 15 mW is being delivered to the node (actual PDL was 14.3 mW), yielding a PTE of 56.9%. A separation distance of approximately 0.8 mm was used in the above experiment using an ABS plastic spacer, the approximate thickness of the human dura mater. To demonstrate the efficiency penalties due to increased coil separation, a PA output power of 23.44 mW (13.7 dBm), a value below the LDO threshold, was used to power a node positioned above the telemetric array using increasing layers of plastic spacers. FIG. 5B shows that as distance increase, the PTE drops significantly. Our design eliminates the issue of coupling distance by transferring power only over the small thickness of the dura. In addition, the effect on coil misalignment was calculated using the PA output power of 23.44 mW (13.7 dBm) and a separation distance of approximately 0.8 mm by moving the node in increments of 1 mm away from the center of the transmitting coil. FIG. 5 C depicts a consistent PTE for misalignment less than 3 mm, but a steep drop in efficiency thereafter. Our results indicate that nodes can move up to 6 mm (3 mm radius) before deleterious loss of transmission efficiency is observed. Additionally, by having multiple coils on the telemetric array, if one coil is not able to sufficiently power a node, a nearby coil with a more appropriate alignment will be able to perform this role. Leveraging techniques such as three-phase inductive powering can be used with adjacent coils to transfer power to a node which is not parallel to the surface of the telemetric array.

Each node must be capable of capturing and digitizing full broadband neural data and passing it onto the wireless data telemetry subsystem. In order to fully capture typical single unit activity, a sample rate of approximately 15 kSps per channel is required. While future nodes will integrate all subsystems into a single ASIC, here we leveraged the Texas Instruments (Dallas, Tex.) ADS7042 analog to digital converter (ADC), which provides an off-the-shelf solution capable of a 1 MSPS sample rate with 12 bit resolution, and uses a SPI interface for simple communication. Additionally, the ADS7042 is available in a package that meets both the size and power constraints required by our design (1.5×1.5 mm; 690 μW).

By multiplexing each channel onto the ADC input, each node is capable of acquiring up to 50 channels of neural data sampled at 20 kSps.

Figure 6:
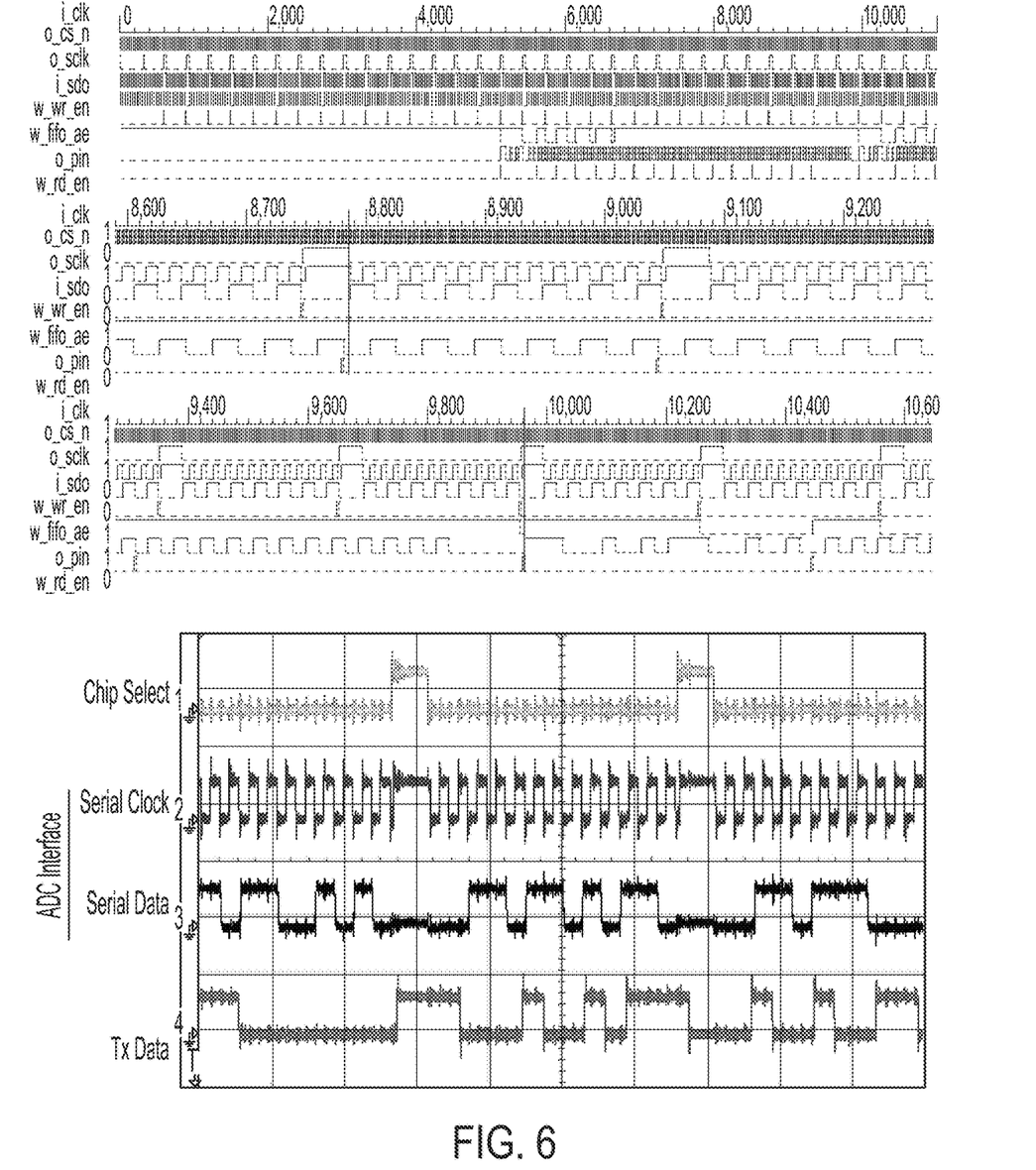
FIG. 6 illustrates exemplary simulation results.

FIG. 6A illustrates simulation results for the circuit implemented on the FPGA. At a start of the simulation 16 samples are captured from the ADC and loaded into a FIFO buffer, a synchronization header is then appended to the packet and sent to the RF transmitter. One full transmission packet is indicated here. The cursor marks the falling edge of the CS signal, capturing a new sample. An 11 bit Barker code is used to synchronize frames in the receiver. From the top down, the ADC chip select signal, serial clock, and serial data signals followed by the data output to be sent to the RF transmit ASIC are shown.

Central control logic is required for multiplexing channels, interfacing with the ADC and telemetry unit, and preparing data for wireless transmission. FPGAs can be programmed to handle each of these tasks and are flexible enough to adapt if peripheral components change. Additionally, FPGAs allow design iterations to be implemented quickly in order to test new encoding or modulation schemes for wireless transmission, or even for on-node processing of acquired data to relieve the processing burden on downstream systems. Given these benefits, each node contains its own iCE40UL1K FPGA (Lattice Semiconductor, Portland, Oreg.), or equivalent fabric in the future. Using development boards, we programmed the iCE40UL1K device to interface with the TI ADC, to organize the data into packets containing 16 samples, and to append a header for synchronization after wireless data transmission. FIG. 6A depicts this process. The system clock is generated using the chip's clk integrated 48 MHz oscillator (i_clk). On the first falling edge of the chip select signal (o_cs_n), the ADS7042 undergoes a self calibration process. Each subsequent falling edge of o_cs_n triggers the ADC to capture a sample. The sampled and digitized data is then clocked out by the falling edges of the serial clock pin (o_sclk) which trigger the ADC to generate each bit of the serial data out signal (i_sclk) containing the digitized data. After all 12 bits of a sample have been read in by the FPGA, the data is written to a first-in-first-out (FIFO) buffer implemented using on-chip block RAM (BRAM). An internal write enable signal (w_wr_en) indicates when each new sample is written to the FIFO. As FIG. 6A shows 16 samples written to the FIFO before any output is sent to the wireless data transmitter (o_pin). The FIFO waits for all 16 samples of the first wireless packet to be captured before clearing an "almost empty" signal (w_ae) which triggers a separate logic module to transmit a synchronization header followed by the serialized data from each of these 16 samples. By using the FIFO in this way, the ADC capture circuitry is isolated from the data transmission circuitry and the protocol or rate of one can change without affecting the other as long as all the data in one packet is written to the transmit chip in the same amount of time it takes to read the next 16 samples from the ADC. Finally, once signaled, the FPGA adds two copies of an 11 bit Barker code (11100010010) as the synchronization header, followed by the 16 packet samples. Each new sample is registered after the previous sample has been transmitted and a read command (w_rd_en) is sent to the FIFO which prepares the next sample. FIG. 6B shows each of these external signals operating as expected in the design. The top trace represents o_cs_n triggering each ADC sample. The middle trace is the o_sclk signal clocking out each bit from the ADC which sends the data in the third trace (i_sdo). The bottom trace is the signal sent to the wireless transmitter and shows the end of the previous packet, followed by a short pause, and the beginning of the next packet containing the synchronization header.

Once the neural signals have been digitized by the ADC and packetized by the FPGA, the data are sent to a printed circuit board containing an ASIC for wireless transmission (FIG. 3D). Data is modulated onto a carrier signal of approximately 3.5 GHz (tunable between 3 and 4 GHz) using on-off shift keying (OOK). This frequency range was specifically chosen to reside outside of other commonly used bands found in a clinical setting therefore reducing potential interference. In addition, it is much higher than the 48.4 MHz signal used for powering the nodes and therefore should not be affected by the wireless powering mechanism. An integrated PA drives an ultra-wide band (3.1-5 GHz) antenna (Fractus Antennas, Barcelona, Spain) through an impedance matching network. Initial prototypes of the neural interrogators support 16 channels of full-spectrum neural data, requiring a baseband data rate of approximately 4.3 Mbps. The transmitter ASIC can send up to 200 Mbps and has been successfully used for transmitting up to 100 channels of neural data 1-2 meters away, using only one quarter of this data rate. As the platform begins to support increasing numbers of interrogators, each node will contain its own transmit chip tuned to a separate frequency channel all communicating with a central wireless receiver. Additional multiplexing techniques, for example code division multiplexing (CDMA), multiple input multiple output (MIMO) techniques, and spatial multiplexing may be evaluated to improve the scalability of the system.

Figure 7:
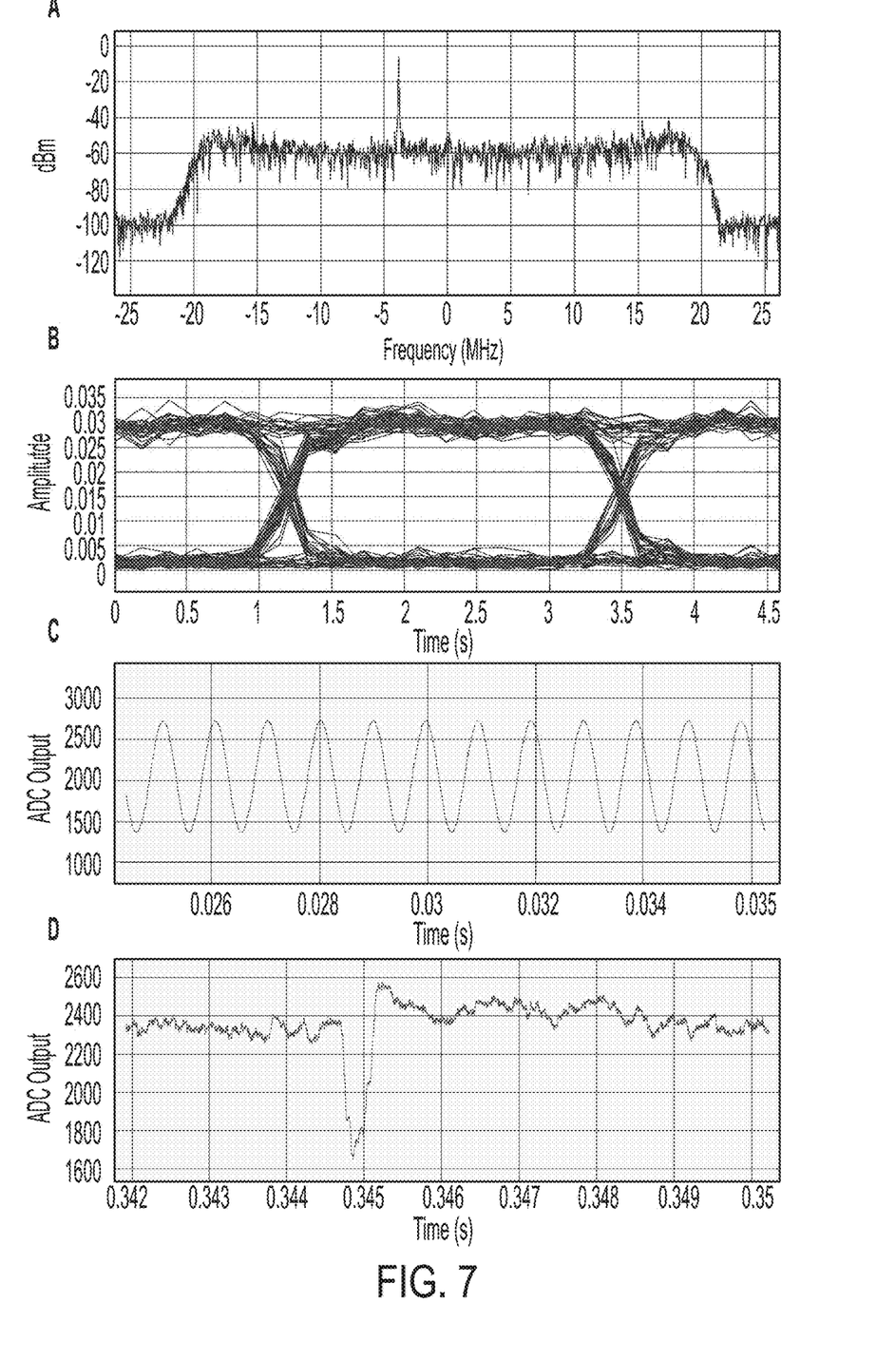
FIG. 7 illustrates exemplary graphs.

The wirelessly transmitted data must be received and demodulated in order to recover the original signal. A software defined radio (SDR) utilizing the AD9361 2×2 transceiver (Analog Devices, Norwood, Mass.) and the Zynq Z-7035 system-on-chip (Xilinx, San Jose, Calif.) was used to build a computer-in-the-loop algorithm in Simulink™ (The MathWorks, Natick, Mass.) for down-mixing the wireless signal, demodulating the OOK data, and sampling each bit. The algorithm searches for the synchronization header and breaks the packet into its constituent samples. The RF front end of the SDR is contained within the AD9361, which first mixes the carrier-modulated data stream down to near-baseband. FIG. 7A shows a spectrum plot generated from the sampled baseband signal captured by the SDR when tuned to 3.5 GHz without any data modulation on the transmitter carrier frequency. From this plot, a small mismatch is observed between the oscillators on the transmit chip and the SDR. Once tuned near the carrier frequency, the SDR generates I and Q samples of the down-converted signal and sends them to a computer, which calculates the magnitude of these complex samples yielding a clean baseband representation of the original modulated data. Fine tuning the baseband sample rate allows for an eye diagram to be generated to evaluate the robustness of the individual symbols received by the SDR (FIG. 7B). Each symbol is represented by approximately 12 baseband samples.

Bit slicing occurs on the host computer which then searches for the header of each packet and converts the samples to 12 bit numbers. The SDR sends frames composed of 640,000 samples of I and Q baseband data. Future work will eliminate the need for the host computer by recovering data directly on the SDR receiver, thereby preventing data loss between frames. Plots C and D of FIG. 7 show the resultant demodulated and decoded signals from one of these frames. In FIG. 7C, a 1 kHz sine wave was played into the ADC using a bench top signal generator. The signal then propagates through each component of the system described above and is successfully reconstructed by the receiver. Similarly, in FIG. 75D, neural data previously recorded from the primary motor cortex of a nonhuman primate walking on a treadmill, was played back from the computer through a digital to analog converter (DAC) into the system and was likewise successfully reconstructed. In both of these examples, bit errors resulting in corrupted data occurred more frequently than desired, but the flexibility of the system allows for future work to explore encoding schemes and other techniques to improve the robustness of the communication. These results demonstrate the feasibility of the platform to capture, digitize, and transmit full-spectrum neural data.

In summary, FIG. 7(A) illustrates a spectrum of the transmitter carrier signal captured from the SDR. The peak value was measured at −6.48 dBm, after RF front end amplification, at 3.82 MHz, indicating a small frequency offset between the oscillators on the transmitter and SDR when both are tuned to 3.5 GHz. (B) illustrates an eye diagram depicting the baseband signal using a sample rate of 52.40985 MHz yielding approximately 12 bits per symbol. Reconstructed samples of both a (C) 1 kHz sine wave and (D) prerecorded neural action potential data from a nonhuman primate walking on a treadmill are illustrated. In these examples, all 16 channels of the packet are being used to encode these data, yielding a sample rate of 320 kSPS. Ultimately this sample rate can be divided to support multiple channels of neural signal acquisition.

Metals and ceramics are among the most widely used rigid packaging materials for chronic device implants in the human body. Titanium and ceramics have, for example, been successfully used in pacemakers, cardiac defibrillators, deep brain stimulators, and cochlear implants (among others) for hermetically sealing active electronic components away from the biological system in which they are implanted; many more materials may be on the horizon. Recently, thin film coatings that combine metals, polymers, and ceramics to seal electronics have been brought from the microelectronics industry and provide micro-thick seals where space is paramount. We propose the use of a highly manufacturable packaging platform that enables simple and direct integration of both existing and future MEAs with hermetically-sealed active electronics.

We utilize a formulation of fused silica that allows for low-temperature seals to be made and thus enables a complete low-temperature fabrication process of the device. For each test structure, two unique fused silica plates were fabricated, one with a 1 mm cavity, and the other at on-which to attach the test circuitry. The silica cavity was aligned with the circuit substrate and boned onto the interposer using a bonding process to form a seal. Nine fused silica cavities were bonded at the same time on the fused silica interposer. After bonding, the fused silica interposer was diced to smaller parts, each with a dimension of 21 mm×21 mm. An elementary immersion test in liquid was performed on the diced parts. No liquid leakage was observed from any of the nine diced parts, demonstrating the gross fidelity of the bond. Long-term evaluation of the fused silica packaging using test circuits with embedded humidity sensors is ongoing.

Figure 8:
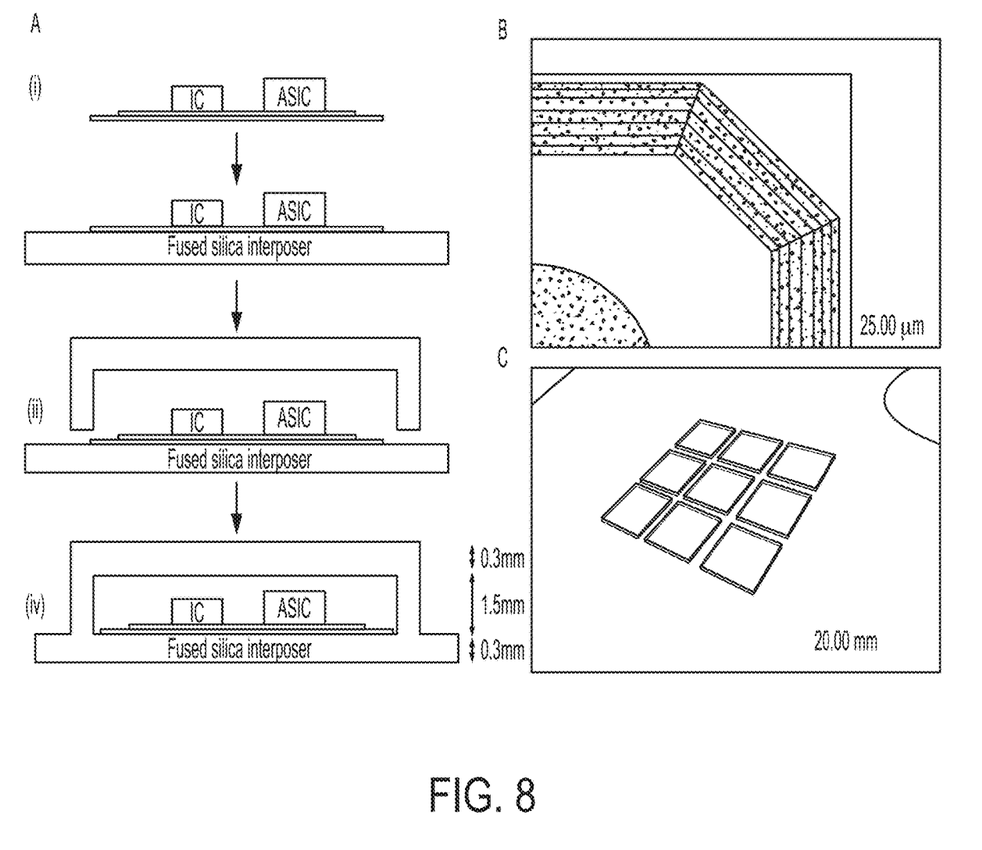
FIG. 8 illustrates exemplary fused silica packaging.

FIG. 8 illustrates exemplary fused silica packaging. (A) shows the step-by-step fabrication and bonding process of the test device (i) The Kapton substrate is pre-patterned with metal traces and contacts using standard micro-fabrication process and was bonded onto a pre-made, thin fused silica sheet (130 um) with adhesives. The substrate is then populated with solder-mounted commercial off-the-shelf (COTS) test components and wire-bonded Application Specific Integration Circuit (ASIC). (ii) The fully-populated substrate is mounted onto a fused silica interposer with adhesives. (iii) A pre-made, fused silica cavity is aligned with the substrate. (iv) A bonding treatment is applied following the perimeter of the cavity so that the cavity bonds onto the interposer forming a water and ion tight seal. The thickness of the fused silica interposer and cavity are indicated in the figure. The final packaged device features a total thickness of 2.1 mm. (B) shows one corner of the cavity after immersion test in liquid. The 7 dark lines are the bond lines used in the bonding process. Light colored area is the reflection from the material interface while dark colored area is the liquid in the interface, which does not penetrate the bond. (C) illustrates an overview picture of the cavities after bonding and dicing.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A system comprises:
   implantable spatially isolated untethered self-contained nodes configured and sized to be located below a dura of a cortical surface or spinal cords each of the implantable spatially isolated untethered self-contained nodes implementing one of a plurality of probe types, the probe types including micro-electrode arrays, micro-ECoG grids, deep brain electrodes and others,
   each of the implantable spatially isolated untethered self-contained nodes configured to record from or stimulate through a plurality of electrodes,
   each of the implantable spatially isolated untethered self-contained nodes comprising onboard logic configured to process electrical signals recorded from individual channels and deliver stimulation pulses to the individual channels, wherein each node has a capacity of a fifty channel maximum of neural data sampled at a sampling rate of at least 15 ksps per channel to capture single unit neural activity;
   a telemetric antenna array configured to be located epidurally, the telemetric antenna array using inductive coupling to provide power to and exchange data with the implantable spatially isolated untethered self-contained nodes wirelessly over a thickness of the dura, eliminating issues of coupling distance; and
   a power and data distribution unit configured to be located epidurally and to power the implantable spatially isolated untethered self-contained nodes, aggregate recorded data, send the aggregated recorded data and commands through a wireless link to an external controller, wherein power transfer efficiency is consistent for up to 6 mm of node movement.

2. The system of claim 1, wherein each of the implantable spatially untethered self-contained isolated nodes comprises reconfigurable logic.

3. The system of claim 2, wherein the logic is data analysis logic.

4. The system of claim 2, wherein the logic is data compression logic.

5. The system of claim 2, wherein the logic is closed loop stimulation logic.

6. The system of claim 2, wherein the logic is configured to implement power saving control schemes.

7. The system of claim 1, wherein each of the implantable spatially untethered self-contained isolated nodes is encapsulated in a package that is RF and optically transparent and robust to ionic diffusion, making a low profile hermetic seal suitable for long term implants.

8. The system of claim 1, wherein a node implements a microelectrode array.

9. The system of claim 1, wherein a node implements a micro-ECoG grid.

10. A method comprising:
providing the system of claim 1; and
recording data from the implantable spatially isolated untethered self-contained nodes untethered from external electronics using the telemetric antenna array to wirelessly power and regulate the implantable spatially isolated untethered self-contained nodes.

11. The method of claim 10, further comprising sending and updating stimulation commands over a wireless link to the implantable spatially isolated untethered self-contained nodes.

12. The method of claim 10, wherein the telemetric antenna array resides above the dura and conforms to a cortical surface.

* * * * *